United States Patent
Ernst et al.

(10) Patent No.: US 10,124,273 B1
(45) Date of Patent: Nov. 13, 2018

(54) PROCESS FOR A DUAL EXTRACT FLUSH

(71) Applicant: UOP LLC, Del Plaines, IL (US)

(72) Inventors: Gregory A. Ernst, Oak Park, IL (US);
Jason L. Noe, Mount Prospect, IL (US); Anton N. Mlinar, Vernon Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/721,888

(22) Filed: Sep. 30, 2017

(51) Int. Cl.
| | | |
|---|---|---|
| *B01D 15/14* | (2006.01) | |
| *C07C 7/12* | (2006.01) | |
| *C07C 25/12* | (2006.01) | |
| *B01D 15/18* | (2006.01) | |
| *C10G 25/12* | (2006.01) | |
| *C07C 15/08* | (2006.01) | |

(52) U.S. Cl.
CPC ......... *B01D 15/1835* (2013.01); *B01D 15/14* (2013.01); *B01D 15/1807* (2013.01); *B01D 15/1842* (2013.01); *C07C 7/12* (2013.01); *C07C 15/08* (2013.01); *C10G 25/12* (2013.01)

(58) Field of Classification Search
None
See application file for complete search history.

(56) References Cited

U.S. PATENT DOCUMENTS

| | | | |
|---|---|---|---|
| 7,977,526 B2 | 7/2011 | Porter | |
| 8,008,536 B2 | 8/2011 | Winter et al. | |
| 8,404,916 B1 * | 3/2013 | Pieper | C07C 7/12 585/820 |
| 8,802,913 B2 | 8/2014 | Porter | |
| 9,024,105 B1 | 5/2015 | Corradi | |
| 9,045,384 B2 | 6/2015 | Corradi et al. | |
| 9,090,523 B1 * | 7/2015 | Horn | C07C 7/04 |
| 2013/0158331 A1 * | 6/2013 | Corradi | B01D 15/1828 585/820 |
| 2014/0170763 A1 * | 6/2014 | Williams | G01N 21/65 436/140 |
| 2015/0376093 A1 * | 12/2015 | Sanders | C07C 7/13 585/828 |
| 2016/0145174 A1 * | 5/2016 | Porter | B01D 15/1807 585/828 |
| 2017/0088489 A1 * | 3/2017 | Salciccioli | C07C 7/04 |
| 2017/0305818 A1 * | 10/2017 | Porter | B01D 15/1835 |

FOREIGN PATENT DOCUMENTS

WO 2016133589 A1 8/2016

* cited by examiner

*Primary Examiner* — Tam M Nguyen

(57) ABSTRACT

The present invention relates to dual extract flush for feeds for xylene extraction processes. More specifically, the present invention relates to dual extract flush for feeds for simulated moving bed extraction processes. It decouples line flush in and line flush out, providing a means for optimizing each flush independently. This scheme will allow for minimizing each bedline and flushing each according to its own bedline volume, which will minimize any additional non-ideal compositions added to the chambers or downstream fractionation.

20 Claims, 1 Drawing Sheet

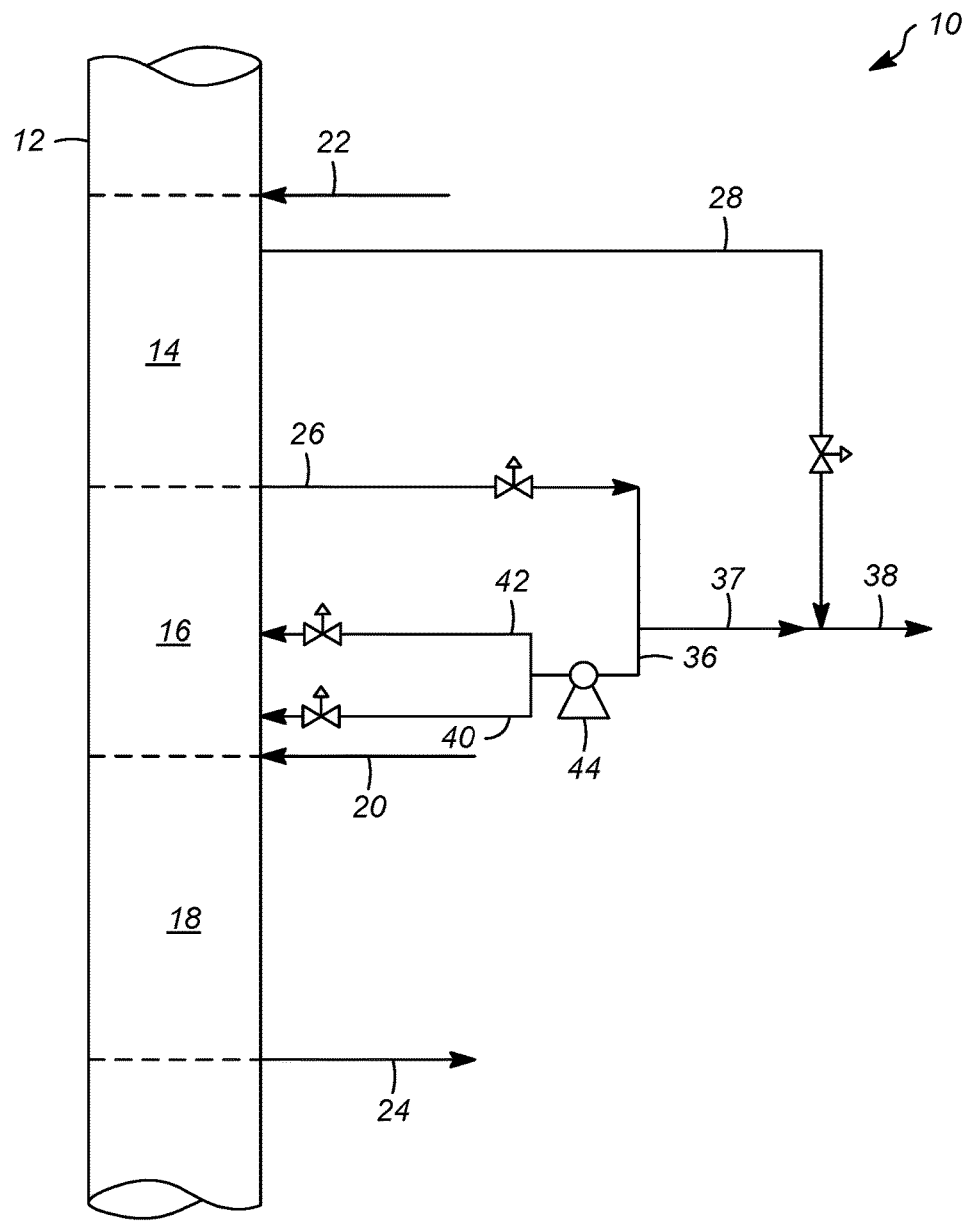

PROCESS FOR A DUAL EXTRACT FLUSH

FIELD

The present invention relates to dual extract flush of feeds for xylene extraction processes. More specifically, the present invention relates to dual extract flush of feeds for xylene extraction processes such as para-xylene extraction or meta-xylene extraction by use of a simulated moving bed.

BACKGROUND

In the para-xylene and meta-xylene simulated bed separation process, and other simulated moving bed separation processes, bedlines are used to carry both extracted and unextracted streams. This means that these bedlines need to be flushed clean of unextracted components before the extracted streams can be withdrawn. If this is not done, the purity of the product will be impacted. In the current practice, the bedline which has been used to carry feed is flushed twice. The first time, after the feed has progressed two bedlines down, the residual feed material is flushed into the chambers and displaced with extract material from the opposite end of the adsorption cycle. The second flush pushes the extract material that is now in the bedline, along with any residual contaminants that weren't flushed initially, to the bed directly below where extract is being withdrawn.

There are several problems with the current practice. First, it couples the requirement of line flush out with the initial line flush in, though these two may not have the same optimal settings (i.e. line flush out may be optimal at approximately 100%, whereas line flush in may be optimal at >100%). Second, it leaves a bedline full of desorbent that will be the first bedline volume worth of material sent to the extract column, which is inefficient for separation, because heat is used to separate this material, though it has already been separated. Third, any feed that remained in the feed bedline is added to the chambers two full beds after the feed goes in, 2-3 minutes after the feed was introduced, at a point where some separation has already occurred, which introduces an inefficiency in feed separation. Finally, any residual contaminants from the feed that remain in the bedline after the first flush are sent to the bed directly below the extract, so there is only one bed of separation to remove these contaminants from the extract.

SUMMARY

The present disclosure encompasses several benefits. It decouples line flush in and line flush out, providing a means for optimizing each flush independently. This scheme will allow for minimizing each bedline and flushing each according to its own bedline volume, which will minimize any additional non-ideal compositions added to the chambers or downstream fractionation. It is also unique as it will use extract material as both the first flush and the second flush. This is important because the remaining bedline material that will be bedline right before it is sent to the extract column will have extract in it, so this will be processed normally by the extract column, without the requirement of additional duty for processing extra desorbent.

Another benefit is that it has the provision for a second flush which will ensure the bedline is clean and send this material to a location between the first flush and the extract where the composition most closely matches what is in the bedline. With the current design with second flush, this is required because of contamination that occurs at the rotary valve due to stepping of the rotary valve. A recent invention prevents this contamination, so second flush for this purpose won't be necessary. The second flush of this design will only be to add what is necessary to keep residual un-flushed contaminants (that remain after the first flush) out of the bedline before it is used to carry extract.

This invention will also incorporate relocation of the over-flushed component of the first flush so that it does not negatively impact adsorptive capacity of adsorbent at the feed point in the column. The current practice is to over-flush the first flush by approximately 20% beyond the bedline volume. This over-flushing introduces desorbent and already-extracted para-xylene into the feed point, which results in a capacity debit. If this 20% over-flush is required for sake of purity, it should be sent to the chambers closer to the extract point, as the material in the beds is closer to that which is in the bedline being flushed. In this way, the impact on capacity will be reduced, or for all practical purposes be eliminated. This will be the purpose of the second extract flush.

In the foregoing, all temperatures are set forth in degrees Celsius and, all parts and percentages are by volume, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE illustrates a dual extract flush for feeds for simulated moving bed extraction processes.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As depicted, process flow lines in the FIGURES can be referred to interchangeably as, e.g., lines, pipes, feeds, gases, products, discharges, parts, portions, or streams.

The term "passing" means that the material passes from a conduit or vessel to an object.

The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication.

The "control system" is defined as hardware and software computing components that determines the set points of control elements in the adsorption section.

The term "Zone 1" is defined as the zone in the adsorbent chambers below the feed and above the raffinate points, and may also be referred to as the "adsorption zone".

The term "Zone 2" is defined as the zone in the adsorbent chambers below the extract and above the feed points, and may also be referred to as the "purification zone".

The term "Zone 3" is defined as the zone in the adsorbent chambers below the desorbent and above the extract points, and may also be referred to as the "desorption zone".

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURE. The FIGURE is a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to a process for dual extract flush 10. As shown in the FIGURE, a process 10 comprises of a unit 12 comprising an adsorption zone 18, a purification zone 16 and a desorption zone 14. In simulated moving bed technologies such as, but not limited to, those for para-xylene separation, each zone and the location of each stream that is added or withdrawn from a chamber moves in succession down through the unit 12, and once it reaches the bottom of unit 12, is sent back to the top of unit 12. The relative positions of each zone and stream remains the same relative to all other zones and streams. In the example shown in the FIGURE, the adsorption zone 18 is located in unit 12 between the feed 20 and raffinate 24, the purification zone 16 is located in unit 12 between the extract 26 and feed 20, and the desorption zone 14 is located in unit 12 between the desorbent 22 and extract 26. The adsorption zone includes a feed 20 and a raffinate 24. The raffinate exits the unit 12 at the bottom of the adsorption zone 18. The feed 20 enters the unit 12 at the top of the adsorption zone 18. The purification zone 16 includes an extract 26 that exits the unit 12 at the top of the purification zone 16, and a first flush 40 and a second flush 42. The first flush 40 is located below the second flush 42. Here, the extract 26 exits the unit 12 and is sent to an extract column by line 38. Line 38 is joined by a line flush out 28 and a portion is taken as line 36 to pump 44.

The extract stream 26 includes a portion 37 that is sent to the extract column, and the remaining stream 36 is sent to a pump 44. Stream 38 that is sent to the extract column also includes the line flush 28 that exits the unit 12 in the desorption zone 14 below the desorbent 22.

Once the extract stream 36 passes through the pump 44, it is divided into two flush lines. The first flush 40 pumped from line 36 and sent to a bedline in the unit 12 immediately after it was used to bring feed into the chamber. The bedline still contains feed, and these remaining feed components will be flushed into the chamber, to send them into the chamber as closely as possible to the location where feed is entering the chamber. This flush will be set to flush approximately 80-100% of the bedline volume during a single step, with little or no allowance for over-flushing, as over flushing at this location introduces a capacity debit. The flushing flow rate will be controlled by a control system.

Additional flushing is required for sake of product purity. This additional flush should be sent into the purification zone closer to the extract point, as the composition in the beds near that point are more enriched in both desorbent and the desired component. Current practice is to send this material 1 bed below the extract. However, in this invention, the over-flushed amount will have a higher concentration of feed contaminants that may cause contamination of the extract product. The rate of this flush should be low, just enough to clear residual feed components. It is contemplated that this may be approximately 20-50% of a bedline volume. This estimate is taken from modeling work that suggests 120-130% of a bedline volume needs to be flushed with flushing material to clear the entire bedline of feed contaminants. Therefore, the remaining required flush, after the initial 80-100% of bedline flush is done with the first flush 40, will accomplished by the second flush 42 later in the purification zone 16.

The first flush 40 enters the unit 12 in the purification zone 16 below the second flush line 42 which also enters the unit 12 in the purification zone 16. In one contemplated example, the first flush 40 may comprise 80% of the total flushing amount required and the second flush 42 may comprise 20% of the total flushing amount required. In another contemplated example, the first flush 40 may comprise 70% of the total flushing amount required and the second flush 42 may comprise 30% of the total flushing amount required. In another contemplated example, the first flush 40 may comprise 60% of the total flushing amount required and the second flush 42 may comprise 40% of the total flushing amount required. In yet another contemplated example, the first flush 40 may comprise 50% of the total flushing amount required and the second flush 42 may comprise 50% of the total flushing amount required. However, it is also contemplated that other combinations of line flushes may be used.

It is contemplated that the first flush 40 will be located in the purification zone 16 one bedline above the feed 20. It is contemplated that the second flush 42 will be located in the purification zone 16 about 2 beds to about 4 beds above the feed 20.

Implementing this invention would represent a large economic benefit. It will reduce the amount of desorbent component in extract stream 38 that needs to be separated in the extract column. Also, it will increase the adsorptive capacity of the adsorbent in unit 12.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for a dual extract flush, comprising passing a feed and desorbent into a unit wherein the unit comprises a desorption zone, a purification zone, and an adsorption zone wherein the desorption zone is located between the desorbent and extract, the purification zone is located between the extract and feed, and the adsorption zone is located between the feed and raffinate; removing an extract from the unit and splitting a portion of the extract stream into a first flush and a second flush; and passing the first flush and the second flush back to the unit. An embodiment of the invention is one, any or all of prior embodiments in this paragraph up through the first embodiment in this paragraph, wherein the unit is a para-xylene extraction unit. An embodiment of the invention is one, any or all of prior embodiments in this paragraph up through the first embodiment in this paragraph, wherein the unit is a meta-xylene extraction unit. An embodiment of the invention is one, any or all of prior embodiments in this paragraph up through the first embodiment in this paragraph, wherein the feed enters the unit at a meeting point of the purification zone and the adsorption zone. An embodiment of the invention is one, any or all of prior embodiments in this paragraph up through the first embodiment in this paragraph, wherein the extract is removed from the unit a meeting point of the desorption zone and the purification zone. An embodiment of the invention is one, any or all of prior embodiments in this paragraph up through the first embodiment in this paragraph, wherein the first flush enters the unit below the second flush. An embodiment of the invention is one, any or all of prior embodiments in this paragraph up through the first embodiment in this paragraph, wherein the first flush and the second flush enter the unit above the feed but below the extract. An embodiment of the invention is one, any or all of prior embodiments in this paragraph up through the first embodiment in this paragraph, wherein the first flush may comprise 70% of the flush and the second flush may comprise 30% of the flush. An embodiment of the invention is one, any or all of prior embodiments in this paragraph up through the first embodiment in this paragraph, wherein the first flush may comprise 60% of the flush and the second flush may comprise 40% of the flush. An embodiment of the invention is one, any or all of prior embodiments in this paragraph up through the first embodiment in this paragraph, wherein the first flush may comprise 80% of the flush and the second flush may comprise 20% of the flush. An embodiment of the invention is one, any or all of prior embodiments in this paragraph up through the first embodiment in this paragraph, wherein the first flush and the second flush are controlled by a control system. An embodiment of the invention is one, any or all of prior embodiments in this paragraph up through the first embodiment in this paragraph, wherein the first flush and the second flush may be controlled independently. An embodiment of the invention is one, any or all of prior embodiments in this paragraph up through the first embodiment in this paragraph, further comprising combining the extract product stream from the unit, with a line flush out and sending this combined stream to an extract column. An embodiment of the invention is one, any or all of prior embodiments in this paragraph up through the first embodiment in this paragraph, wherein the unit comprises a plurality of beds, and the second flush enters the unit two to four beds above the feed. An embodiment of the invention is one, any or all of prior embodiments in this paragraph up through the first embodiment in this paragraph, wherein the unit comprises a plurality of beds, and the first flush enters the unit one bed above the feed. An embodiment of the invention is one, any or all of prior embodiments in this paragraph up through the first embodiment in this paragraph, further comprising a third flush that may be split from the extract product stream from the unit and sent back to the unit in the purification zone. An embodiment of the invention is one, any or all of prior embodiments in this paragraph up through the first embodiment in this paragraph, wherein the third flush may enter the unit in between the second flush and the extract.

A second embodiment of the invention is a process for a dual extract flush, comprising passing a feed and a desorbent to a unit comprising a plurality of beds wherein the unit comprises a desorption zone, a purification zone, and an adsorption zone wherein the desorption zone is located between the desorbent and extract, the purification zone is located between the extract and feed, and the adsorption zone is located between the feed and raffinate; removing an extract from the unit; splitting the extract stream into a first flush and a second flush; and passing the first flush and the second flush back to the unit wherein the first flush may comprise 70% of the flush and the second flush may comprise 30% of the flush. An embodiment of the invention is one, any or all of prior embodiments in this paragraph up through the second embodiment in this paragraph, wherein the unit comprises a plurality of beds, and the second flush enters the unit below the extract and two to four beds above the feed. An embodiment of the invention is one, any or all of prior embodiments in this paragraph up through the second embodiment in this paragraph, wherein the unit comprises a plurality of beds, and the first flush enters the unit below the extract one bed above the feed.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for a dual extract flush, comprising:
    passing a feed and desorbent into a unit wherein the unit comprises a desorption zone, a purification zone, and an adsorption zone wherein the desorption zone is located between the desorbent and extract, the purification zone is located between the extract and feed, and the adsorption zone is located between the feed and raffinate;
    removing an extract from the unit and splitting a portion of the extract stream into a first flush and a second flush; and
    passing the first flush and the second flush back to the unit.

2. The process of claim 1, wherein the unit is a paraxylene extraction unit.

3. The process of claim 1, wherein the unit is a metaxylene extraction unit.

4. The process of claim 1, wherein the feed enters the unit at a meeting point of the purification zone and the adsorption zone.

5. The process of claim 1, wherein the extract is removed from the unit at a meeting point of the desorption zone and the purification zone.

6. The process of claim 1, wherein the first flush enters the unit below the second flush.

7. The process of claim 1, wherein the first flush and the second flush enter the unit above the feed but below the extract.

8. The process of claim 1, wherein the first flush may comprise 70% of the flush and the second flush may comprise 30% of the flush.

9. The process of claim 1, wherein the first flush may comprise 60% of the flush and the second flush may comprise 40% of the flush.

10. The process of claim 1, wherein the first flush may comprise 80% of the flush and the second flush may comprise 20% of the flush.

11. The process of claim 1, wherein the first flush and the second flush are controlled by a control system.

12. The process of claim 1, wherein the first flush and the second flush may be controlled independently.

13. The process of claim 1, further comprising combining the extract product stream from the unit, with a line flush out and sending this combined stream to an extract column.

14. The process of claim 1, wherein the unit comprises a plurality of beds, and the second flush enters the unit two to four beds above the feed.

15. The process of claim 1, wherein the unit comprises a plurality of beds, and the first flush enters the unit one bed above the feed.

16. The process of claim 11, further comprising a third flush that may be split from the extract product stream from the unit and sent back to the unit in the purification zone.

17. The process of claim 16, wherein the third flush may enter the unit in between the second flush and the extract.

18. A process for a dual extract flush, comprising:
    passing a feed and a desorbent to a unit comprising a plurality of beds wherein the unit comprises a desorption zone, a purification zone, and an adsorption zone wherein the desorption zone is located between the desorbent and extract, the purification zone is located between the extract and feed, and the adsorption zone is located between the feed and raffinate;
    removing an extract from the unit;
    splitting the extract stream into a first flush and a second flush; and
    passing the first flush and the second flush back to the unit wherein the first flush may comprise 70% of the flush and the second flush may comprise 30% of the flush.

19. The process of claim 18, wherein the unit comprises a plurality of beds, and the second flush enters the unit below the extract and two to four beds above the feed.

20. The process of claim 18, wherein the unit comprises a plurality of beds, and the first flush enters the unit below the extract one bed above the feed.

* * * * *